United States Patent
Kitahara et al.

(10) Patent No.: US 9,964,478 B2
(45) Date of Patent: May 8, 2018

(54) DESTRUCTIVE INSPECTION METHOD AND QUALITY DETERMINATION METHOD FOR VITREOUS SILICA CRUCIBLE

(71) Applicant: SUMCO CORPORATION, Minato-ku, Tokyo (JP)

(72) Inventors: Ken Kitahara, Akita (JP); Tadahiro Sato, Akita (JP); Toshiaki Sudo, Akita (JP); Eriko Kitahara, Akita (JP); Takashi Watanabe, Akita (JP)

(73) Assignee: SUMCO CORPORATION, Tokyo (JP)

( * ) Notice: Subject to any disclaimer, the term of this patent is extended or adjusted under 35 U.S.C. 154(b) by 0 days. days.

(21) Appl. No.: 15/512,535

(22) PCT Filed: Sep. 24, 2015

(86) PCT No.: PCT/JP2015/076951
§ 371 (c)(1),
(2) Date: Mar. 17, 2017

(87) PCT Pub. No.: WO2016/047694
PCT Pub. Date: Mar. 31, 2016

(65) Prior Publication Data
US 2017/0292901 A1    Oct. 12, 2017

(30) Foreign Application Priority Data
Sep. 22, 2014    (JP) .................. 2014-192923

(51) Int. Cl.
*G01N 19/08*    (2006.01)
*G01N 3/307*    (2006.01)
(Continued)

(52) U.S. Cl.
CPC ............ *G01N 3/307* (2013.01); *C03B 19/095* (2013.01); *C30B 15/10* (2013.01); *C30B 29/06* (2013.01);
(Continued)

(58) Field of Classification Search
CPC ............ G01N 3/307; G01N 2203/001; G01N 2203/0035; G01N 2203/0064; C03B 19/095; C30B 15/10; C30B 29/06
(Continued)

(56) References Cited

U.S. PATENT DOCUMENTS 9,809,902 B2 *   11/2017  Sudo ................. C30B 15/26
2002/0017144 A1 *  2/2002  Miles ................. G01N 3/32
                                                    73/808

(Continued)

FOREIGN PATENT DOCUMENTS

JP    H0854384 A    2/1996
JP    H11228283 A   8/1999
(Continued)

OTHER PUBLICATIONS

International Search Report (ISR) dated Nov. 2, 2015, issued for International application No. PCT/JP2015/076951.

*Primary Examiner* — Max Noori
(74) *Attorney, Agent, or Firm* — Law Office of Katsuhiro Arai (57) ABSTRACT

A destructive inspection method of a vitreous silica crucible for pulling a silicon single crystal evaluates a crack state of an inner surface of the vitreous silica crucible supported by a graphite susceptor when a load is instantaneously applied to at least one point on the inner surface via an automatic center punch while pushing the tip portion of the automatic center punch against the inner surface. The destructive inspection method can inspect the vitreous silica crucible under conditions as close to the actual conditions of use as possible.

12 Claims, 9 Drawing Sheets

(51) Int. Cl.
  *C30B 29/06* (2006.01)
  *C30B 15/10* (2006.01)
  *C03B 19/09* (2006.01)

(52) U.S. Cl.
  CPC .......... *G01N 2203/001* (2013.01); *G01N 2203/0035* (2013.01); *G01N 2203/0064* (2013.01)

(58) Field of Classification Search
  USPC .......................................................... 73/799
  See application file for complete search history.

(56) References Cited

U.S. PATENT DOCUMENTS

| | | | |
|---|---|---|---|
| 2006/0117866 A1* | 6/2006 | Myers | G01N 3/32 73/837 |
| 2007/0205791 A1* | 9/2007 | Ahmad | G01R 31/2817 73/862.474 |
| 2011/0069313 A1* | 3/2011 | Sakai | G01N 21/9505 356/369 |
| 2012/0167821 A1* | 7/2012 | Sudo | C30B 35/002 117/200 |

FOREIGN PATENT DOCUMENTS

| | | |
|---|---|---|
| JP | 2010241620 A | 10/2010 |
| JP | 2012017243 A | 1/2012 |
| JP | 2013512186 A | 4/2013 |
| JP | 2013095650 A | 5/2013 |
| JP | 2013139353 A | 7/2013 |
| WO | 2011066336 A1 | 6/2011 |

* cited by examiner

| | The Second arc | Power consumption of the last arc discharge | Arrangement of points where the impact of the destructive inspection of the present application is applied | Crack state of the inner surface of the crucible in the destructive inspection of the present application | Breakage of the crucible in the destructive inspection of the present application | Determination of the destructive inspection of the present application | Breakage of the crucible (made under the same condition) during use in the CZ pulling |
|---|---|---|---|---|---|---|---|
| Crucible A of the first arc | None | 764kWh | On straight line | Only impression | None | Good | None |
| | | | On circumference | Only impression | None | Good | None |
| Crucible B of the first arc | | 712kWh | On straight line | Only impression | None | Good | None |
| | | | On circumference | Only impression | None | Good | None |
| Crucible C of the first arc | | 680kWh | On straight line | Only impression | None | Good | None |
| | | | On circumference | Only impression | None | Good | None |
| Crucible D of the first arc | | 638kWh | On straight line | Small | None | Slightly good | None |
| | | | On circumference | Small | None | Slightly good | None |
| Crucible P of the second arc | Yes | 184kWh | On straight line | Small | None | Slightly good | None |
| | | | On circumference | Small | None | Slightly good | None |
| Crucible Q of the second arc | | 137kWh | On straight line | Slightly large | None | Slightly poor | None |
| | | | On circumference | Slightly large | None | Slightly poor | None |
| Crucible R of the second arc | | 103kWh | On straight line | Large crack | Broken | Poor | Broken during filling the polysilicon |
| | | | On circumference | Large crack | Broken | Poor | Broken during filling the polysilicon |
| Crucible S of the second arc | | 64kWh | On straight line | Large crack | Broken | Poor | Broken during filling the polysilicon |
| | | | On circumference | Large crack | Broken | Poor | Broken during filling the polysilicon |
| Annealed crucible | Yes (crucible of the second arc) | 64kWh | On straight line | Only impression | None | Good | None |
| | | | On circumference | Only impression | None | Good | None |

DESTRUCTIVE INSPECTION METHOD AND QUALITY DETERMINATION METHOD FOR VITREOUS SILICA CRUCIBLE

This application is the U.S. National Phase under 35 U.S.C. § 371 of International Application PCT/JP2015/076951, filed Sep. 24, 2015, which claims priority to Japanese Patent Application No. 2014-192923, filed Sep. 22, 2014. The International Application was published under PCT Article 21(2) in a language other than English.

TECHNICAL FIELD

The present disclosure relates to a destructive inspection method and a quality determination method of a vitreous silica crucible, and in particular, to a destructive inspection method and a quality determination method of a vitreous silica crucible using an automatic center punch.

BACKGROUND

In the manufacture of a silicon single crystal by the Czochralski method (CZ method), a vitreous silica crucible is used. In the CZ method, silicon raw material is charged into the vitreous silica crucible and heated to melt. Then, a seed crystal is dipped into this silicon melt, and the seed crystal is gradually pulled up while rotating the crucible to grow a single crystal. In order to manufacture a silicon single crystal at low cost, it is necessary to improve the single crystal yield at one time of pulling process. For this purpose, it is necessary to use a large capacity crucible capable of holding a large amount of raw material.

In the preparatory stage of pulling the silicon single crystal by the CZ method, raw material blocks of polycrystalline silicon are filled in the vitreous silica crucible in advance. This filling operation is performed manually, and the raw material blocks are packed carefully one by one so that no impact will be applied to the crucible. At this time, the operation takes about 1 hour in the case of CZ pulling of a silicon single crystal having a diameter of 300 mm, for example. The vitreous silica crucible is very delicate and a breakage or a defect is easily generated. This is because the vitreous silica crucible is easily broken when a large amount of raw material is introduced vigorously. Further, in order to obtain as large a silicon single crystal ingot as possible at one time of pulling process, it is necessary to first fill as much raw material as possible in the crucible without gaps. For that purpose, a careful filling operation is required in consideration of the size, the shape and the like of the raw material blocks. Patent Document 1 describes a method of filling raw material blocks of polycrystalline silicon. In this filling method, the first layer of polycrystalline silicon blocks is formed in the crucible, and the second layer of polycrystalline silicon blocks is formed on the first layer. The height of the first layer is made lower than the height of the melt surface after all the polycrystalline silicon raw material has been melted, and the outer periphery of the second layer is separated from the inner peripheral surface of the crucible.

However, even if a careful filling operation is performed manually, a phenomenon where the vitreous silica crucible is broken suddenly during filling the small pieces of polycrystalline silicon is seen. When the vitreous silica crucible is broken, not only the crucible itself cannot be used, but also the filling operation of the raw material that has been done so far is wasted, resulting in a very large loss in terms of cost and man-hour. Such breakage is hard to be prevented completely, but it is possible to know the type and condition of an easily broken crucible, and the problem can be avoided by treating the easily broken crucible as a defective product. For that purpose, it is necessary to inspect the vitreous silica crucible in a condition as close as possible to the actual status of use.

As an inspection method of a vitreous silica crucible, for example, Patent Document 2 describes an optical nondestructive inspection method of inspecting bubbles existing in the inner surface of the vitreous silica crucible by using optical detecting means and image processing means. Further, Patent Document 3 describes a crucible inspection method of inspecting only the impurities contained in the outermost surface layer of the crucible inner surface, by specifying the impurity component from the wavelength and intensity of the fluorescence generated by laser light irradiation and calculating the content of the impurities. In addition, Patent Document 4 describes a method of inspecting an abnormal site in a vitreous silica crucible. In the method, at least one of an infrared absorption spectrum and a Raman spectrum is measured at a measurement point on the crucible inner surface, and whether or not an abnormal site such as brown ring or the like is generated at the measurement site is judged based on the obtained spectrum. Further, Patent Document 5 describes a method of obtaining the hardness of a silica sintered body crucible from the force of a release point after a load was continuously applied. In Patent Document 5, the hardness of a crucible is defined by pressing force.

PRIOR ART REFERENCE

Patent Documents

Patent Document 1: Japanese Patent Application Laid-Open No. 2010-241620
Patent Document 2: Japanese Patent Application Laid-Open Hei No. 11-228283
Patent Document 3: Japanese Patent Application Laid-Open No. 2012-17243
Patent Document 4: Japanese Patent Application Laid-Open No. 2013-139353
Patent Document 5: Japanese Patent Application Laid-Open No. 2013-95650

SUMMARY

Problems to be Solved by the Disclosure

Impact fracture of glass can be roughly divided into: bending fracture in which the fracture is initiated by the acting of tensile stress on an opposite surface being subjected to impact by bending; and Hertzian fracture in which a pressure is applied intensively to an impact surface by an impact of a small hard body, so that a conical fracture surface is formed and the fracture is initiated.

A so-called shot-bag test is known as a destructive inspection method of glass by bending fracture. The shot-bag test is a test in which a weight is swung downward like a pendulum, and collided with a glass surface to apply an impact. When a shot-bag test is performed on a vitreous silica crucible, a broken state of the crucible inner surface caused by collision of the pendulum weight against the crucible inner wall surface is evaluated.

A so-called Hertzian fracture test is known as a destructive inspection method of glass by Hertzian fracture. Hertzian fracture test is a test in which a small diameter cylindrical rod of ultra-hard material is collided with a glass end surface. When a Hertzian fracture test is performed on a vitreous silica crucible, a Hertzian crack state of the crucible inner surface caused by collision of the cylindrical rod against the crucible bottom surface is evaluated.

Generally, the impact fracture strength of the glass is complicatedly affected by the material and the weight of the object applying the impact, the speed of applying the impact, the shape of the contact surface, the size and the shape of the glass, the position where the impact is applied, the installation status of the glass, or the like.

Bending fracture occurs when the impacted area is large and the impact speed is slow. On the other hand, Hertzian fracture occurs when the impacted area is small and the impact speed is fast. Since the actual polycrystalline silicon block has very sharp pointed corners, the area where the impact acts on the crucible is small. On the other hand, in the actual preparatory stage of pulling the silicon single crystal by the CZ method, raw material blocks of polycrystalline silicon are carefully packed manually one by one in the vitreous silica crucible so as not to give impact to the vitreous silica crucible, so that the speed of impact applied to the vitreous silica crucible is slow. That is, when filling the polycrystalline silicon raw material in the vitreous silica crucible, the area where the impact acts is small and the impact speed is slow, so to speak, it is in an intermediate state between the bending fracture and the Hertzian fracture.

Therefore, there is a problem that the broken state of the vitreous silica crucible inner surface is greatly different between those caused by these destructive tests and those caused by actually filling with the raw material blocks of polycrystalline silicon. In addition, since the crucible has a curved surface, the position where the impact is perpendicularly imparted to the crucible inner wall surface and the load are not stable, it is necessary to change the posture according to the evaluation portion so that the pendulum can easily hit a crucible having a diameter of 800 mm, and as a result, there is a problem that the test facility is also large-sized. Although there is a method of dropping an iron ball to give an impact, there is a problem that the situation when filling the polysilicon raw material in the crucible can not be reproduced.

Furthermore, in order to evaluate the ease-of-breaking of the vitreous silica crucible, the inventors of the present disclosure disposed an air cylinder at the diameter portion of the crucible and quietly applied a pressure of 2 MPa. But the crucible was not broken at all and the evaluation was not suitable. Thus, no test method for reproducing the phenomenon where the vitreous silica crucible is broken suddenly during filling the raw material has been known.

Therefore, an object of the present disclosure is to provide a destructive inspection method of a vitreous silica crucible and a quality determination method of a vitreous silica crucible using the destructive inspection method, wherein the destructive inspection method is capable of inspecting in a state as close as possible to a situation in which a raw material block is actually filled in the vitreous silica crucible.

Means for Solving the Problem

In order to solve the above-mentioned problems, the destructive inspection method of the vitreous silica crucible according to the present disclosure, evaluates the crack state of an inner surface of the vitreous silica crucible for pulling a silicon single crystal when a load is instantaneously applied to one point on the inner surface via an automatic center punch while pushing a tip portion of the automatic center punch against the inner surface.

According to the present disclosure, it is possible to provide a new inspection method capable of reproducing a phenomenon where the vitreous silica crucible is broken suddenly during filling the raw material blocks. In particular, a certain load can be easily applied to an arbitrary point on the crucible inner surface, and the ease-of-breaking of the vitreous silica crucible can be easily and accurately determined. Therefore, by feeding back the determination result to the manufacturing process, it is possible to manufacture a vitreous silica crucible which is hard to break and has high reliability.

The destructive inspection method according to the present disclosure, preferably evaluates a crack state of the inner surface when a load is instantaneously applied to a plurality of points on a line along the inner surface from the center of a bottom portion of the vitreous silica crucible toward an upper end of a rim via the automatic center punch. Thereby, it is possible to easily and accurately determine the portion where the vitreous silica crucible is easily broken. Therefore, by feeding back the result of the determination to the manufacturing process (arc melting speed, arc melting time, cooling speed, etc.), it is possible to manufacture a vitreous silica crucible which is hard to break and has high reliability.

The destructive inspection method according to the present disclosure, preferably evaluates a crack state of the inner surface when a load is instantaneously applied to a plurality of points along an inner surface on a circle at a certain distance from the center of the bottom portion of the vitreous silica crucible via the automatic center punch.

In the present disclosure, the magnitude of the load is preferably 50 N or more and 400 N or less, more preferably 200 N or more and 400 N or less, and even more preferably 250 N or more and 350 N or less. No sufficient cracks for the evaluation are generated in the vitreous silica crucible in the case of less than 50 N, and a cone-shaped hole is opened in the vitreous silica in the case of exceeding 400 N. This is because cracks that can be formed are not generated in the vitreous silica crucible during filling the raw material. That is, if the magnitude of the load falls within this numerical value range, a load equivalent to the load actually applied to the inner surface of the crucible can be given.

Advantageous Effects of the Disclosure

According to the present disclosure, it is possible to easily and accurately determine the ease-of-breaking of a vitreous silica crucible, in particular, it is possible to provide a destructive inspection method of a vitreous silica crucible and a quality determination method of a vitreous silica crucible using the destructive inspection method, wherein the destructive inspection method is capable of inspecting in a state as close as possible to the actual status of use.

DESCRIPTION OF DRAWINGS

FIG. 6 is a table showing the result of a destructive inspection on the vitreous silica crucible.

DETAILED DESCRIPTION

Hereinafter, preferred embodiments of the present disclosure will be described in detail with reference to the accompanying drawings.

Figure 1:
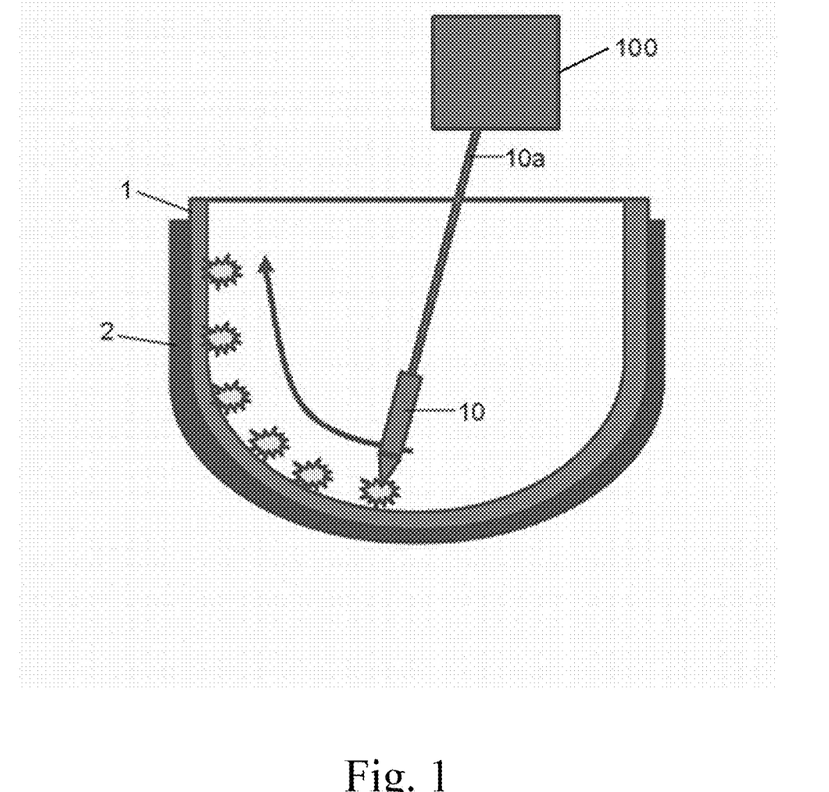
FIG. 1 is a schematic view for explaining an inspection method of a vitreous silica crucible according to a preferable embodiment of the present disclosure.

FIG. 1 is a schematic view for explaining an inspection method of a vitreous silica crucible according to a preferable embodiment of the present disclosure.

As shown in FIG. 1, the destructive inspection method of the vitreous silica crucible according to the present embodiment, evaluates the crack state of an inner surface of a vitreous silica crucible 1 when a load is applied by an automatic center punch 10 to the inner surface. A plurality of measurement points are set at predetermined intervals on a measurement line extending from a center of a bottom portion of the crucible toward an upper end of a rim of the crucible, and a load is applied to the inner surface of the crucible at each measurement point, so that the ease-of-breaking and an easily broken portion of the crucible can be specified.

In the manufacture of a silicon single crystal by the CZ method, a large amount of raw material blocks of polycrystalline silicon are filled in the vitreous silica crucible, and these raw material blocks are heated to melt, so that a silicon melt is generated. Since the polycrystalline silicon block has a very sharp pointed corner, the corner is brought into pressure contact with one point on the inner surface of the crucible, and raw material blocks are further stacked thereon, whereby a flaw is generated at one point on the inner surface of the crucible. On the other hand, if the crack progresses to this position when the tensile residual strain in the vitreous silica constituting the crucible is large, the tensile residual stress is released and the crack further expands so that a large crack is generated on the inner surface of the crucible, and proceeds to the rim portion of the crucible or the end portion of the already existing crack, and the crucible is destroyed. The destructive inspection method of the vitreous silica crucible according to the present embodiment is a method that evaluates the ease-of-breaking of the crucible by reproducing the load applied to the inner surface of the crucible during filling such raw material.

The vitreous silica crucible used for manufacturing a silicon single crystal by the CZ method includes a bottom portion, a cylindrical straight body portion, an opaque vitreous silica layer containing a large number of microbubbles, a transparent vitreous silica layer crucible without bubbles on the inner surface side, and a very rough quartz powder sintered layer (crucible outer surface layer) formed on the surface of the opaque vitreous silica layer. In this way, the wall body of the crucible has a multilayer structure including a plurality of layers having different characteristics with respect to the thickness direction thereof.

Although the size of the crucible is not particularly limited, since a larger-sized vitreous silica crucible has a larger capacity in proportion to its size, a large amount of raw material can be filled. For example, it is possible to hold about 357 kg of silicon raw material (silicon melt) for a 28-inch crucible, about 529 kg of silicon raw material for a 32-inch crucible, about 670 kg of silicon raw material for a 36-inch crucible and about 938 kg of silicon raw material for a 40-inch crucible, respectively. In this way, since a very large load is applied to the inner surface of the crucible as a large amount of raw material is packed in the crucible, and fissures tend to occur, the effect of the present disclosure becomes larger as the crucible having a larger capacity. Therefore, the destructive inspection method according to the present invention is suitable for inspecting a vitreous silica crucible having an opening diameter of 800 mm (32 inches) or more.

The wall thickness of the crucible varies more or less depending on the portion (straight body portion, curved portion, bottom portion) or the diameter, and is preferably 8 to 15 mm, especially about 10 mm. That is, the destructive inspection method according to the present disclosure is neither a method for inspecting an extremely thin vitreous silica material of 5 mm or less, nor a method for inspecting an extremely thick vitreous silica material of 50 mm or more. In particular, in the present disclosure, the vitreous silica crucible of which a bottomed cylindrical shape is maintained is the object of destructive inspection, and a fragment cut out from the vitreous silica crucible is not an inspection object. This is because the crucible having a cylindrical straight body portion and a curved bottom portion and the opening portion of the upper end of the rim being shaped by cutting, has an internal residual stress due to being restricted over the entire circumference, so that the fragment cut out from the vitreous silica crucible may be broken even under conditions that a breakage is not generated, and it is necessary to perform the inspection under conditions that are extremely similar to the actual status of use.

In toughened glass, while a compressive residual stress is applied to the glass surface to strengthen the surface, the tensile residual stress is strongly applied to the inside of the glass, so that when the crack reaches this portion, the crack progresses and becomes shattered. Since the vitreous silica crucible also has compressive residual stress and tensile residual stress, the crack tends to proceed. The vitreous silica crucible has a cylindrical shape at the upper portion and a curved surface at the lower portion, and the end portion of the rim is a circular edge, while a plate glass has edges through all the periphery of the glass surface, so the residual stress of the vitreous silica crucible is different from that of the plate glass. In addition, the distribution of the wall thickness is not constant, and it may differ by nearly twice in the upper portion and the lower portion. Further, a two-layer structure having a synthetic vitreous silica layer made of synthetic silica powder on the inner surface side and a natural vitreous silica layer made of natural quartz powder on the outer surface side is generally used, and from the difference of the physical property values such as density or the like of respective layer, the distribution of residual stress is extremely complex.

As shown in FIG. 1, the vitreous silica crucible 1 is inspected in a state of being accommodated in the graphite susceptor 2. Since the vitreous silica crucible 1 is used in the state of being accommodated in the graphite susceptor 2 in the manufacture of the silicon single crystal, and the filling of the raw material is also performed in a state in which the vitreous silica crucible 1 is supported by the graphite susceptor 2, it is possible to perform the inspection under conditions close to the actual status of use by inspecting the vitreous silica crucible 1 in the state of being accommodated in the graphite susceptor 2.

The automatic center punch 10 is a tool for reproducing the load applied to the inner surface of the crucible when a large amount of raw material blocks have been filled in the crucible. The polycrystalline silicon block has a very sharp pointed corner, and this pointed corner abuts the inner surface of the crucible. When more raw materials are packed in the crucible and the load applied to the inner surface of the crucible increased, the crucible will be broken. Since the automatic center punch 10 acts as a pointed corner of the polycrystalline silicon block, it is possible to easily create an inspection condition close to the actual status of use.

The hardness of the tip portion of the automatic center punch 10 abutting the inner surface of the crucible is required to be equal or higher than the hardness of the silicon raw material. The modified Mohs hardness of silicon is "7". The modified Mohs hardness of the electric melting quartz is "7", while the vitreous silica crucible of the present application adopts an arc melting method and the manufacturing method is different. The modified Mohs hardness of the tip portion of the automatic center punch 10 is required to be "7" or more, and preferably "8" or more.

For example, the tip of the automatic center punch may be a hard metal such as tungsten carbide or a diamond tip. The shape of the tip may be a conical shape like a Rockwell indenter or a pyramidal shape like a Vickers indenter. If the tip portion is damaged, the impact will not be properly transferred to the vitreous silica and the variation in the test result will be large, which is not appropriate.

As shown in FIG. 1, the automatic center punch 10 is attached to a tip portion of a supporting rod 10a attached to a movable device 100 such as a 6-axis robot or the like, and it is preferably to press the automatic center punch 10 against the inner surface of the crucible via the supporting rod 10a. The large-sized crucible has a large opening diameter which is a diameter of 800 mm, a deep depth of 500 mm or more, and the distance to the inner bottom surface is long, so that the pressing operation can be easily performed by using such a supporting rod 10a.

Figure 2:
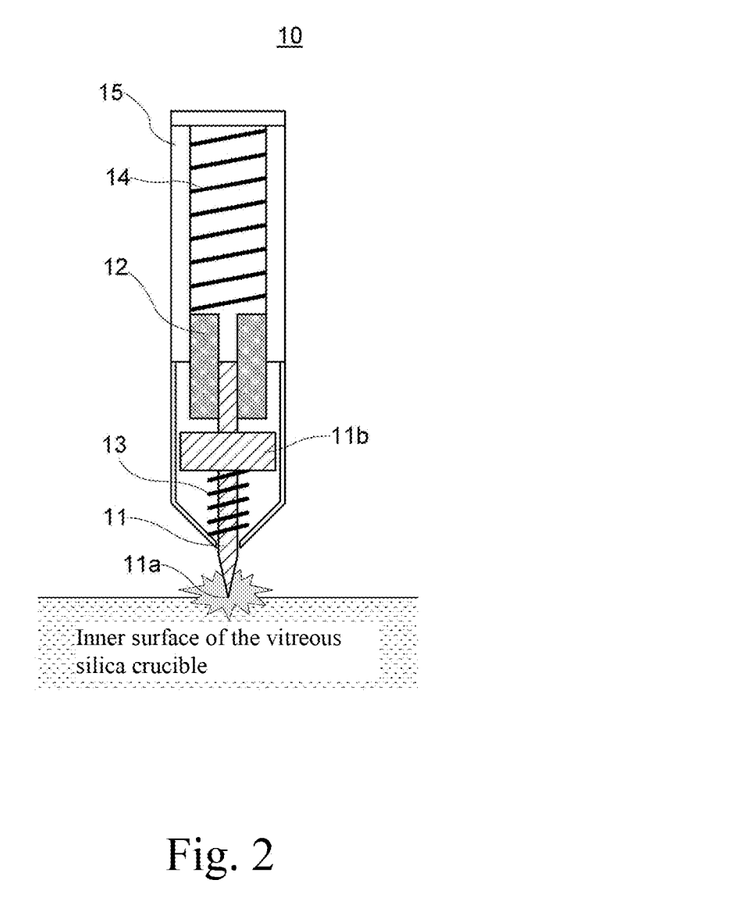
FIG. 2 is a schematic sectional view showing one example of a structure of an automatic center punch 10.

FIG. 2 is a schematic sectional view showing one example of a structure of an automatic center punch 10.

As shown in FIG. 2, the automatic center punch 10 includes: a shaft 11 made of a rod-shaped metal member having a pointed tip; a hammer portion 12 provided at a rear end portion of the shaft 11; a coil spring 13 energizing the shaft 11 in the rear end direction thereof; a coil spring 14 provided at a rear end portion of the hammer portion 12; and a substantially cylindrical case 15 for accommodating them. The tip portion 11a of the shaft 11 is projected from the opening of the tip portion of the case 15. The automatic center punch 10 can instantaneously apply a large load to an object in contact with the tip portion 11a of the shaft 11. The amount of the load of the automatic center punch 10 is preferably 50 to 400 N, more preferably 200 to 400 N, and even more preferably 250 to 350 N. Further, the load may be an instantaneous load which reaches the maximum peak from about zero within a range of 1/3000 second to 1/250 second.

By hitting the hammer portion 12 out with the adjustable coil spring 14, the hammer portion 12 applies an impact to a flange portion 11b of the shaft 11, and this impact is transferred to the inner surface of the vitreous silica crucible through the shaft 11. The load of the shaft 11 is instantaneously removed by the coil spring 13 provided on the tip side of the shaft 11.

As a result of applying such impact, depending on the crucibles, some crucibles are broken and others are not broken. However, it is possible to provide a high quality crucible which is hard to break by investigating the way of generating the crack as the reason that caused the broken crucibles, and adjusting the arc melting process.

As described above, the destructive inspection method of the vitreous silica crucible according to the present embodiment, can evaluate the quality of the crucible under a condition closer to that in actual usage of the crucible, because the broken state of the inner surface of the crucible is evaluated when an impact is given and a larger load is applied by the automatic center punch 10 after abutting the tip portion of the automatic center punch 10 on the inner surface of the crucible at a certain load in the same manner as placing the corner of the polycrystalline silicon block on the inner surface of the crucible.

As mentioned above, the preferred embodiments of the present disclosure have been described. The present disclosure is not in particular limited to the above-mentioned embodiments, and various modifications are possible as long as the modification does not depart from the spirit of the present disclosure, and those modifications are within the scope of the present disclosure.

For example, in the above-mentioned embodiment, the measurement is performed at a predetermined interval along the longitudinal direction from the center of the bottom portion of the vitreous silica crucible to the upper end of the rim, but the present disclosure is not limited to such measurement and a measurement may be performed at a predetermined interval in the circumferential direction, for example.

EXAMPLES

Figure 3:
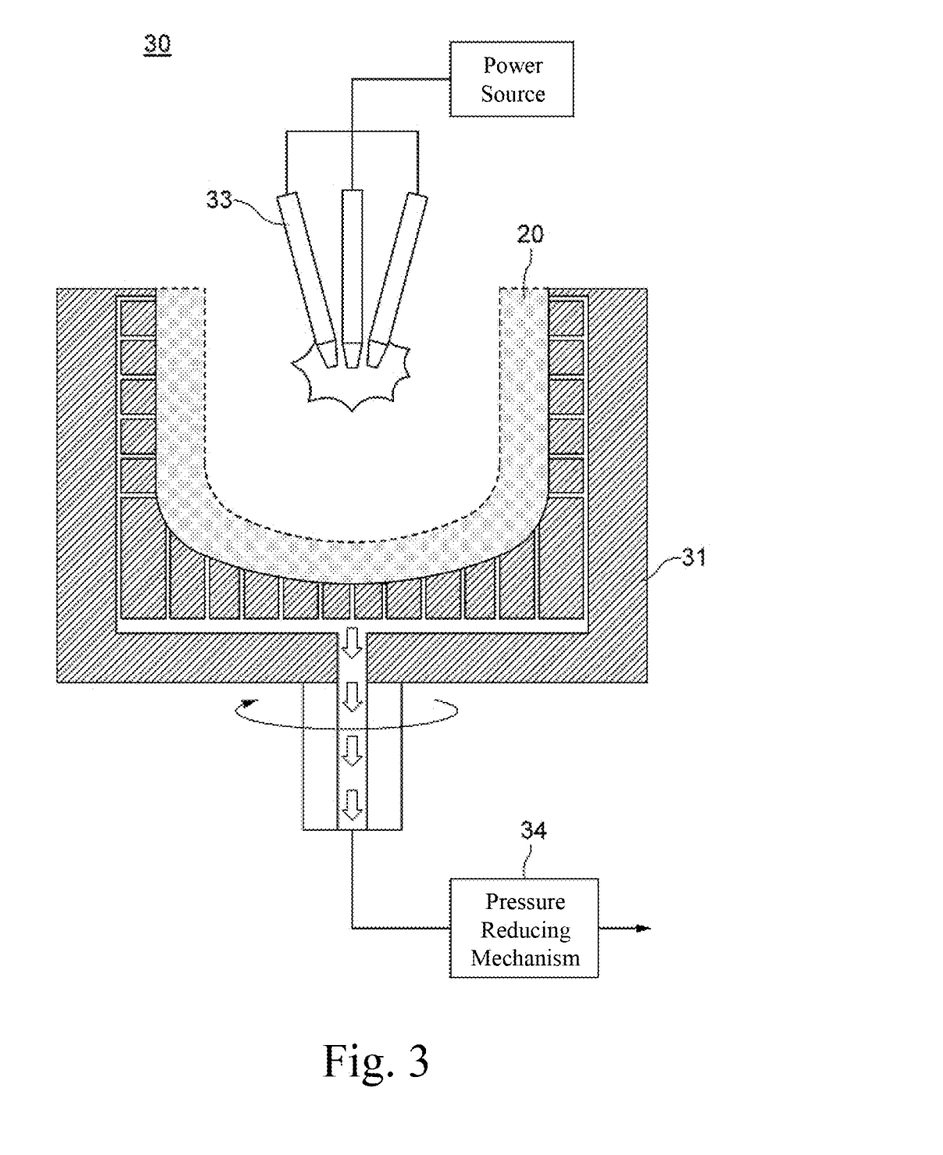
FIG. 3 is a schematic view of an arc melting device.

A vitreous silica crucible was manufactured by using the arc melting device 30 in FIG. 3. In the manufacturing of the crucible, raw material quartz powder 32 was filled in a rotating carbon crucible mold (mold 31), and the quartz powder 32 was molded into a crucible shape using a jig. Next, the quartz powder 32 was heated to melt (step S1 in FIG. 4) by the first arc discharge (the first arc melting process) due to an arc electrode 33 while operating the pressure reducing mechanism 34 to deaerate with the mold 31 being rotated, and then cooled to obtain a vitreous silica crucible. Further, the upper end surface of the crucible was cut to adjust the height, and chamfered. A vitreous silica crucible which has no problem as a product through examining the inner surface was designated as a "crucible of the first arc" (step S2 in FIG. 4).

Figure 4:
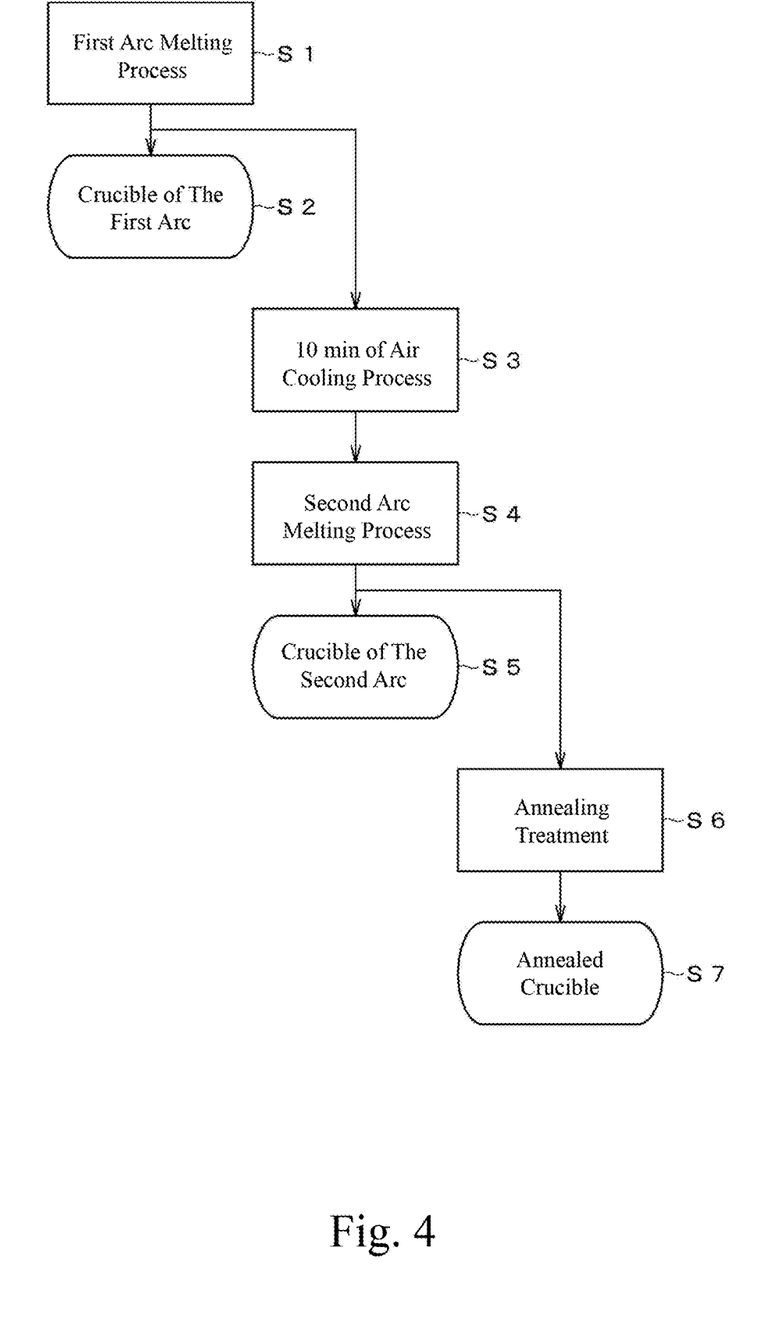
FIG. 4 is a flowchart showing a crucible manufacturing process.

After completion of the first arc melting process, the inner surface was heated by the second arc discharge (the second arc melting process) after a cooling process of 10 minutes (step S3 in FIG. 4) to change the inner surface structure (step S4 in FIG. 4). Thereafter, the crucible was cooled, and the crucible in a state of being usable as a product was designated as a "crucible of the second arc" (step S5 in FIG. 4).

Further, the crucible of the second arc was subjected to an annealing treatment at about 1100° C. for about 1 hour to relax the residual strain in the vitreous silica (step S6 in FIG. 4). Thereby, the annealed vitreous silica crucible was designated as an "annealed crucible" (step S7 in FIG. 4).

Since the power consumption during the arc discharge is important for determining the magnitude of the residual strain of the vitreous silica crucible, four "crucibles of the first arc" and four "crucibles of the second arc" were respectively prepared (A, B, C, D, P, Q, R, S, respectively)

by changing the amount of electric power consumed in the last arc discharge. The conditions of the first arc when manufacturing the crucible of the second arc were all the same as those of the crucible A of the first arc. Further, the conditions of the first and second arcs during manufacturing the annealed crucible were the same as the condition of the crucible S of the second arc.

Specifically, among the crucibles of the first arc, the power consumption of the "crucible A of the first arc" was 764 kWh, the power consumption of the "crucible B of the first arc" was 712 kWh, the power consumption of the "crucible C of the first arc" was 680 kWh, and the power consumption of the "crucible D of the first arc" was 638 kWh. Also, among the crucibles of the second arc, the power consumption at the time of the first arc is the same as that of the crucible A, the power consumption of the "crucible P of the second arc" was 184 kWh, the power consumption of the "crucible Q of the second arc" was 137 kWh, the power consumption of the "crucible R of the second arc" was 103 kWh, and the power consumption of the "crucible S of the second arc" was 64 kWh. Further, the annealed crucible was designated as a crucible annealed to be the "crucible S of the second arc". The arc conditions are shown in FIG. 6.

Figure 5:
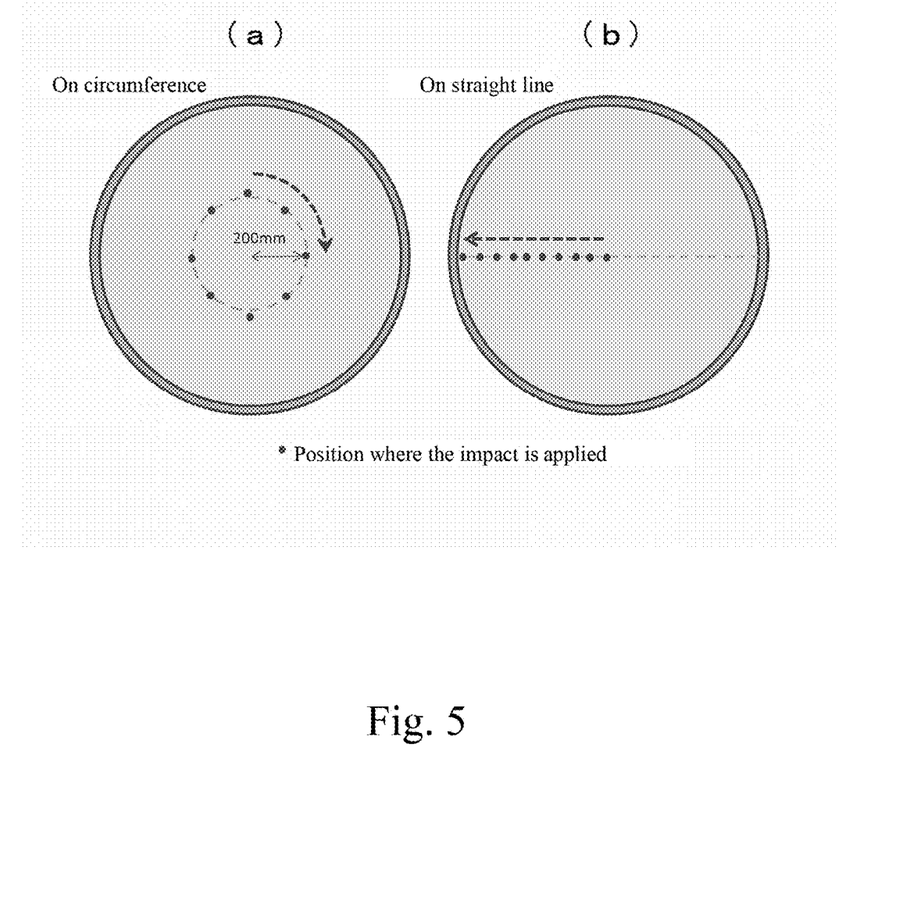
FIG. 5 is a view showing one example of arrangement of points where the impact is applied to the inner surface of a crucible.

The destructive inspection according to the present disclosure was performed with respect to a vitreous silica crucible having an opening diameter of 800 mm. As shown in FIG. 5, the crucible samples to be inspected are prepared by making two crucibles for each of the above 9 kinds of crucibles, and the points where the impact is applied are made in two ways: on the circumference with a radius of 200 mm shown in (a); and on the straight line shown in (b).

Next, six automatic center punches A to F were prepared, and the load of the automatic center punch was measured by using a load cell twice with respective to A and B, and once with respective to C to F. As a result, as shown in A to F of FIG. 7, it was found that a load of 50 N or more and 400 N or less can be applied to these automatic center punches.

Figure 7:
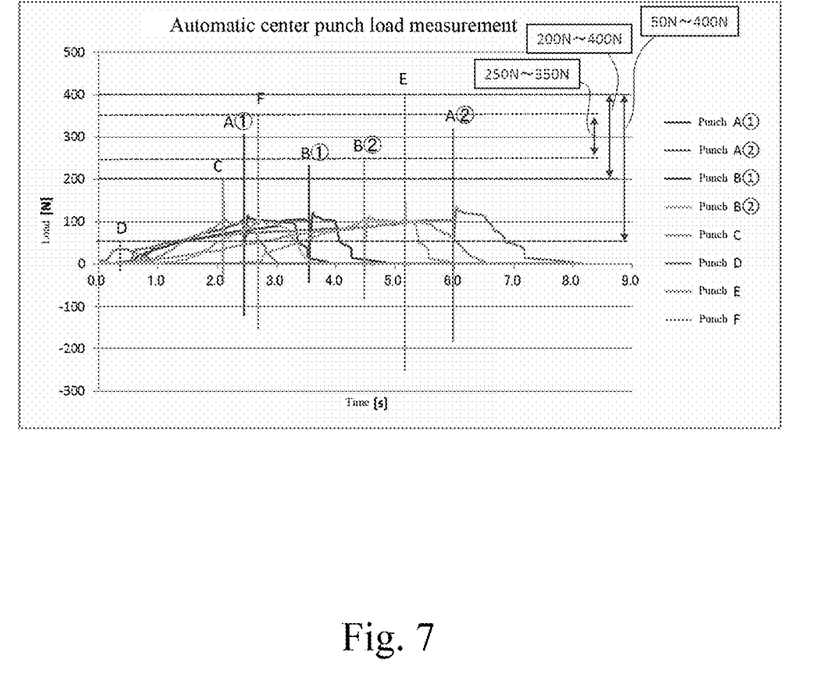
FIG. 7 is a graph showing the results of measuring the load of the automatic center punch eight times.
Figure 8:
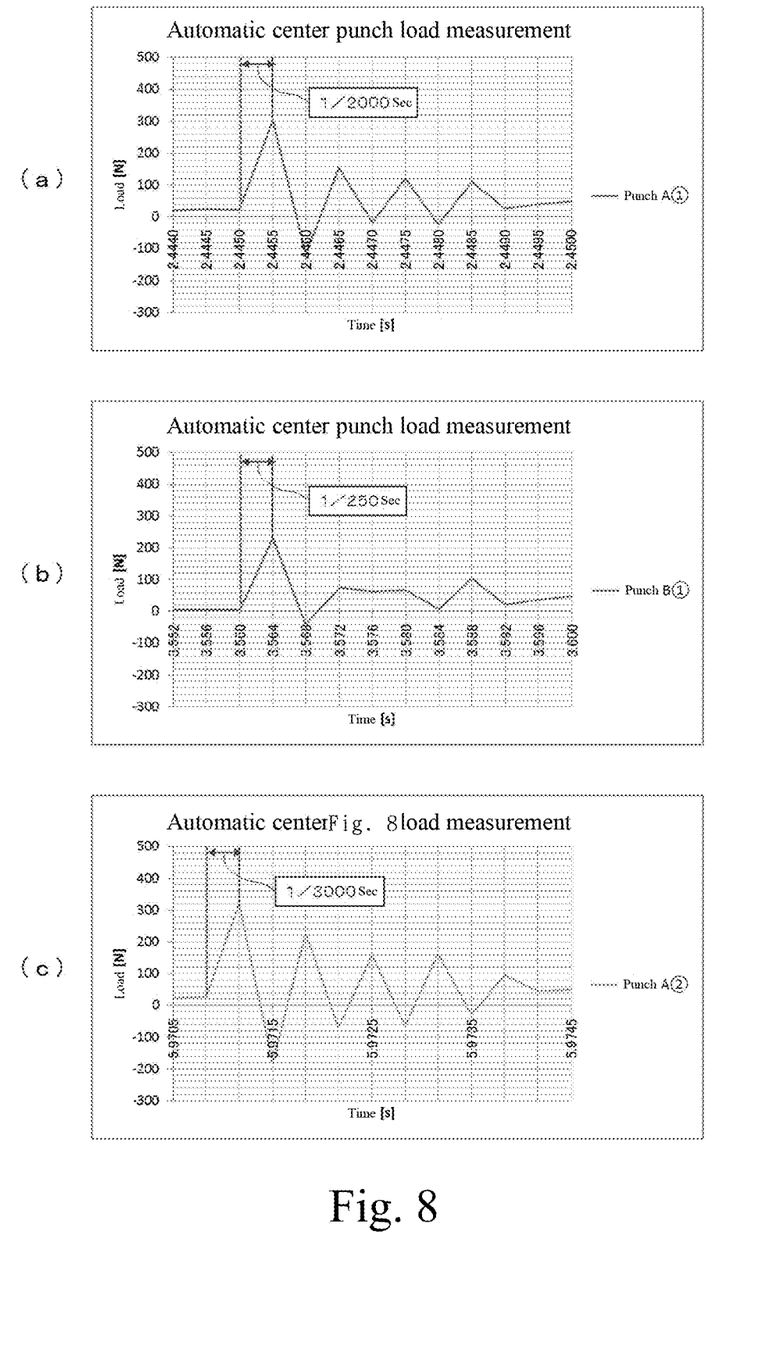
FIG. 8 is a graph showing in detail one of the measurement results of FIG. 7.

FIGS. 8(a) to 8(c) show the measurement results shown in FIG. 7 in more detail. As shown in FIG. 8(a), it can be seen that for the automatic center punch A (1) (indicated by a circled numeral 1 in the figure, and the same applies hereinafter), about 300 N is reached after 0.0005 sec (1/2000 sec) from the time of 2.4450 [S] from the start of the measurement and then a drop to about −120 N occurs after 0.0005 sec. Also, as shown in FIG. 8(b), it can be seen that for the automatic center punch B (1), about 220 N is reached after 0.004 sec (1/250 sec) from the time of 3.560 [S] from the start of the measurement, and then a drop to about −40 N occurs after 0.04 sec. Also, as shown in FIG. 8(c), it can be seen that for the automatic center punch A (2), about 320 N is reached after 0.0003 sec (1/3000 sec) from the time of 5.9709 [S] from the start of the measurement, and then a drop to about −180 N occurs after 0.0003 sec. Thereby, the automatic center punch is a tool that can apply an instantaneous load (impact force) instead of a gentle load.

Next, a destructive inspection using the automatic center punch was performed on the sample of the above mentioned vitreous silica crucible, and the result thereof was visually evaluated.

As a result, as shown in FIG. 6, in the crucibles A, B and C of the first arc, a small impression remained at the point where the impact was applied, but no crack occurred. Also, only a small impression remained in the annealed crucible, and no crack occurred.

On the other hand, in the crucible D of the first arc and the crucible P of the second arc, small cracks of several millimeters originating from impressions occurred. Also, a crack of about 1 cm which was slightly larger than those of the above two crucibles occurred in the crucible Q of the second arc.

Figure 9:
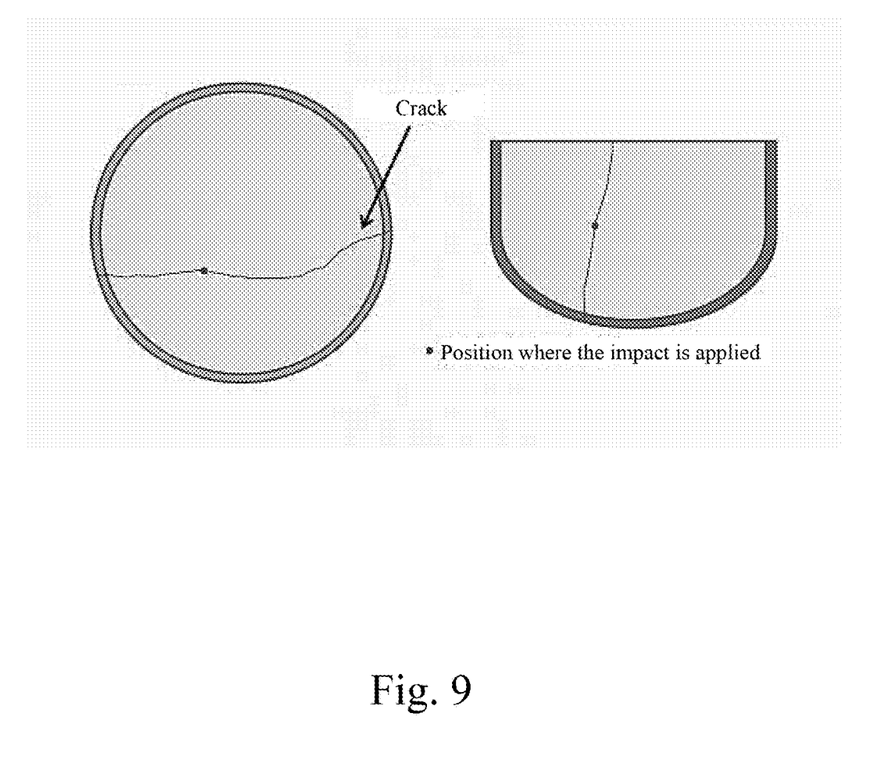
FIG. 9 is a view showing a crack state of a crucible S of the second arc in a destructive inspection.

The cracks generated by a single impact in the crucibles R and S of the second arc were larger than those of the other crucibles, and the crucibles are broken as the cracks reached the end surface of the rim of the crucible from the point where the impact was implied. The crack state of the crucible S of the second arc is shown in FIG. 9.

EXPLANATION OF REFERENCE SYMBOLS 1 vitreous silica crucible
2 graphite susceptor
10 automatic center punch
10a supporting rod
11 shaft
11a tip portion
11b flange portion
12 hammer portion
15 case
30 arc melting device
31 mold
32 quartz powder
33 arc electrode
34 pressure reducing mechanism
100 movable device

What is claimed is:

1. A destructive inspection method of a vitreous silica crucible, characterized by evaluating a crack state of an inner surface of a vitreous silica crucible for pulling a silicon single crystal when a load is instantaneously applied to at least one point on the inner surface via an automatic center punch while pushing a tip portion of the automatic center punch against the inner surface.

2. The destructive inspection method of the vitreous silica crucible according to claim 1, which evaluates a crack state of the inner surface when a load is instantaneously applied, via the automatic center punch, to a plurality of points, respectively, along a line on the inner surface extending from a center of a bottom portion of the vitreous silica crucible toward an upper end of a rim.

3. The destructive inspection method of the vitreous silica crucible according to claim 1, which evaluates a crack state of the inner surface when a load is instantaneously applied, via the automatic center punch, to a plurality of points, respectively, along a circle on the inner surface at a given distance from the center of a bottom portion of the vitreous silica crucible.

4. The destructive inspection method of the vitreous silica crucible according to claim 1, wherein a magnitude of the load is 50 N or more and 400 N or less.

5. A quality determination method of a vitreous silica crucible, using the destructive inspection method according to claim 1.

6. The destructive inspection method of the vitreous silica crucible according to claim 2, wherein a magnitude of the load is 50 N or more and 400 N or less.

7. The destructive inspection method of the vitreous silica crucible according to claim 3, wherein a magnitude of the load is 50 N or more and 400 N or less.

8. A quality determination method of a vitreous silica crucible, using the destructive inspection method according to claim 2.

9. A quality determination method of a vitreous silica crucible, using the destructive inspection method according to claim 3.

10. A quality determination method of a vitreous silica crucible, using the destructive inspection method according to claim 4.

11. A quality determination method of a vitreous silica crucible, using the destructive inspection method according to claim 6.

12. A quality determination method of a vitreous silica crucible, using the destructive inspection method according to claim 7.

\* \* \* \* \*